US008595028B2

(12) United States Patent
Green, III et al.

(10) Patent No.: US 8,595,028 B2
(45) Date of Patent: *Nov. 26, 2013

(54) SYSTEM AND METHOD FOR PERFORMING MEDICAL RESEARCH ACROSS A VAST PATIENT POPULATION

(75) Inventors: W. Thomas Green, III, Carrollton, GA (US); James T. Ingram, Carrollton, GA (US); Johnathan Samples, Woodland, AL (US); Gregory H. Schulenburg, Carrollton, GA (US); Jason Colquitt, Carrollton, GA (US); Steve Felt, Hamilton, GA (US)

(73) Assignee: Greenway Medical Technologies, Inc., Carrollton, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/082,761

(22) Filed: Apr. 8, 2011

(65) Prior Publication Data
US 2011/0264466 A1    Oct. 27, 2011

Related U.S. Application Data

(63) Continuation of application No. 12/392,998, filed on Feb. 25, 2009.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS 3,597,742 A    8/1971  Philipps et al.
4,491,725 A    1/1985  Pritchard (Continued)

FOREIGN PATENT DOCUMENTS

EP    0808882 A2    11/1997
EP    1086997 A2    3/2001

(Continued)

OTHER PUBLICATIONS http://www.ihe.net/Technical_Framework/upload/IHE_ITI_TF_Suppl_RFD_TI_2006_09_25.pdf.*

(Continued)

*Primary Examiner* — Robert Morgan
*Assistant Examiner* — Maroun Kanaan
(74) *Attorney, Agent, or Firm* — Blank Rome LLP

(57) ABSTRACT

A system and method for performing medical research over an extended computer network is disclosed. The system and method comprise a plurality of Electronic Health Record (EHR) systems configured to capture patient data for a plurality of general patients at a plurality of corresponding healthcare provider sites during encounters with those patients, a research system configured to generate one or more electronic documents for completion with patient data that is related to the medical research, and an enhanced services server built on the same architecture as the plurality of EHR systems, wherein the one or more electronic documents include one or more first fields and one or more second fields for completion with patient data that is related to the medical research and the enhanced services server is in electronic data communication with the plurality of EHR systems and the one or more research systems via a network connection. Qualifying patients are identified from among the plurality of general patients and the first fields in each of the electronic documents are automatically populated with patient data for a corresponding qualifying patient. The one or more electronic documents that were automatically populated with patient data is electronically transmitted to at least one EHR system via the network connection, and the at least one EHR system is used to complete the second fields in each of the electronic documents during subsequent patient encounters. The completed electronic documents are electronically transmitted from the at least one EHR system to the enhanced services server, which electronically transmits the completed electronic documents back to the research system via the network connection.

24 Claims, 5 Drawing Sheets

(56) References Cited

U.S. PATENT DOCUMENTS

| | | |
|---|---|---|
| 4,987,538 A | 1/1991 | Johnson et al. |
| 5,065,315 A | 11/1991 | Garcia |
| 5,205,861 A | 4/1993 | Matrick |
| 5,267,155 A | 11/1993 | Buchanan et al. |
| 5,359,509 A | 10/1994 | Little et al. |
| 5,361,202 A | 11/1994 | Doue |
| 5,572,422 A | 11/1996 | Nematbakhsh et al. |
| 5,583,758 A | 12/1996 | McIlroy et al. |
| 5,644,778 A | 7/1997 | Burks et al. |
| 5,659,741 A | 8/1997 | Eberhardt |
| 5,664,207 A | 9/1997 | Crumpler et al. |
| 5,704,044 A | 12/1997 | Tarter et al. |
| 5,748,907 A | 5/1998 | Crane |
| 5,758,095 A | 5/1998 | Albaum et al. |
| 5,772,585 A | 6/1998 | Lavin et al. |
| 5,823,948 A | 10/1998 | Ross, Jr. et al. |
| 5,826,237 A | 10/1998 | Macrae et al. |
| 5,827,180 A | 10/1998 | Goodman |
| 5,832,488 A | 11/1998 | Eberhardt |
| 5,845,253 A | 12/1998 | Rensimer et al. |
| 5,857,967 A | 1/1999 | Frid et al. |
| 5,899,998 A | 5/1999 | McGauley et al. |
| 5,903,889 A | 5/1999 | de la Huerga et al. |
| 5,911,687 A | 6/1999 | Sato et al. |
| 5,915,241 A | 6/1999 | Giannini |
| 5,924,074 A | 7/1999 | Evans |
| 5,933,809 A | 8/1999 | Hunt et al. |
| 5,940,802 A | 8/1999 | Hildebrand et al. |
| 5,946,659 A | 8/1999 | Lancelot et al. |
| 5,950,630 A | 9/1999 | Portwood et al. |
| 5,956,690 A | 9/1999 | Haggerson et al. |
| 5,970,466 A | 10/1999 | Detjen et al. |
| 5,991,729 A | 11/1999 | Barry et al. |
| 5,991,730 A | 11/1999 | Lubin et al. |
| 5,995,937 A | 11/1999 | DeBusk et al. |
| 5,995,939 A | 11/1999 | Berman et al. |
| 6,004,276 A | 12/1999 | Wright et al. |
| 6,018,713 A | 1/2000 | Coli et al. |
| 6,024,699 A | 2/2000 | Surwit et al. |
| 6,047,259 A | 4/2000 | Campbell et al. |
| 6,054,505 A | 4/2000 | Gundlach et al. |
| 6,283,761 B1 | 9/2001 | Joao |
| 6,289,316 B1 | 9/2001 | Aghili et al. |
| 6,314,556 B1 | 11/2001 | DeBusk et al. |
| 6,347,329 B1 | 2/2002 | Evans |
| 6,374,229 B1 | 4/2002 | Lowrey et al. |
| 6,603,464 B1 | 8/2003 | Rabin |
| 7,461,079 B2 | 12/2008 | Walker et al. |
| 2001/0023419 A1 | 9/2001 | Lapointe et al. |
| 2001/0041991 A1 | 11/2001 | Segal et al. |
| 2002/0007311 A1 | 1/2002 | Iseki et al. |
| 2002/0073111 A1 | 6/2002 | Heyliger |
| 2002/0103811 A1 | 8/2002 | Fankhauser et al. |
| 2002/0138524 A1 | 9/2002 | Ingle et al. |
| 2004/0010425 A1 | 1/2004 | Wilkes et al. |
| 2004/0128323 A1 | 7/2004 | Walker et al. |
| 2006/0106641 A1 | 5/2006 | Bartsch et al. |
| 2008/0046292 A1* | 2/2008 | Myers et al. ............ 705/3 |
| 2008/0243546 A1 | 10/2008 | Ashford et al. |
| 2009/0080408 A1 | 3/2009 | Natoli et al. |

FOREIGN PATENT DOCUMENTS

| | | |
|---|---|---|
| EP | 1114851 A1 | 7/2001 |
| EP | 1122286 A1 | 8/2001 |
| EP | 1158030 A2 | 11/2001 |
| EP | 1167471 A2 | 1/2002 |
| WO | WO-95/12857 | 5/1995 |
| WO | 0110963 A1 | 2/2001 |
| WO | 0125340 A1 | 4/2001 |
| WO | 0194476 A2 | 12/2001 |

OTHER PUBLICATIONS

IHE, IHE it infrastrcutre technical framework supplement 2006-2007, Aug. 15, 2006 http://www.ihe.net/Technical_Framework/upload/IHE_ITI_TF_Supplement_XDS_Stored_Query_TI_2006_08_15.pdf.*

Bellazzi, Web-based telemedicine systems for home-care; technical issues and experiences, Computer Methods and Programs in Biomedicine, vol. 64, Issue 3, Mar. 1, 2001, pp. 175-187.

Anonymous. Charting eases onto the information highway. Medical Economics. Oradell: Jul. 25, 1994, vol. 71, Isssue 14; p. 82.

Canadian Datasystems. A cure for the paper plague, May 1991, vol. 23, Issue 14; p. D13.

PR Newswire. Homestead.com helps people jump starting their web sites with customizable templates and site building resources, New York: Feb. 7, 2000; p. 1.

Gilnert, Susan, By design adds tools and clip art. Computer Shopper, Jun. 1994, vol. 14, No. 6, p. 494.

Retrieve Form for Data Capture (RFD) http://ww.ihe.net/Participation/upload/iti11₁₃ ihewkshp07_rfd_details_cole.pdf.

Brown et al. "VistaA—U.S. Dept. of Veterans Affairs national-scale HIS"; International Journal of Medical Informatics; pp. 135-156, Mar. 2003.

* cited by examiner

SYSTEM AND METHOD FOR PERFORMING MEDICAL RESEARCH ACROSS A VAST PATIENT POPULATION

CROSS-REFERENCE TO RELATED APPLICATIONS

This application is a continuation of U.S. patent application Ser. No. 12/392,998, filed Feb. 25, 2009, which is related to U.S. patent application Ser. No. 10/202,627, filed Jul. 25, 2002, and U.S. Pat. No. 7,716,072, issued May 11, 2010, the entire contents of which are incorporated herein by reference.

FIELD OF THE INVENTION

This invention relates to systems and methods of utilizing the data captured by an integrated medical software system. More particularly, the present invention relates to systems and methods of utilizing the data captured in an integrated medical software system to conduct medical research, to maintain disease registries, to analyze the quality and safety of healthcare providers, and to conduct composite clinical and financial analytics.

BACKGROUND OF THE INVENTION

Traditionally, healthcare providers have kept all of their patients' information in paper filing systems. That patient information includes, but is not limited to, patients' demographic information (e.g., age, weight, gender, race, income, and geographic location) and health-related information (e.g., clinician documentation of observations, thoughts and actions, treatments administered, patient history, medication and allergy lists, vaccine administration lists, laboratory reports, X-rays, charts, progress notes, consultation reports, procedure notes, hospital reports, correspondence, and test results). The healthcare providers that keep that patient information include, but are not limited to, physicians—Doctor of Medicine (MD) or Doctor of Osteopathic Medicine (DO), dentists, chiropractors, podiatrists, therapists, psychologists, physician assistants, nurses, medical assistants, and technicians.

The manual, paper-based practice of keeping a patient's information, however, is a very inefficient, labor-intensive process requiring many checks and balances to ensure accurate processing of the information and requiring a significant amount of the healthcare provider's time that could otherwise be spent with the patient. Accordingly, electronic medical records (EMRs), Electronic Health Records (EHRs), and Personal Health Records (PHRs) have been developed to provide many of the functionalities and features of paper filing systems in an electronic, paperless format. Systems using EMRs, EHRs, and PHRs have been developed to streamline clinical, financial, and administrative information; to streamline workflow processes; and to improve coding and billing accuracy.

An EMR is an electronic record of patient information that can be created, gathered, managed, and consulted by the authorized clinicians and staff at the specific healthcare provider that creates the record. An EHR is an electronic record of patient information that conforms to nationally recognized interoperability standards and that can be created, managed, and consulted by authorized clinicians and staff at the healthcare provider that creates the record as well as those at other healthcare provider sites. And, a PHR is an electronic record of patient information that conforms to nationally recognized interoperability standards and that can be drawn from multiple sources while being managed, shared, and controlled by the patient to whom it belongs. Accordingly, EMRs are aimed primarily at the efficient management of multiple records in a single healthcare provider's practice, while EHRs and PHRs are aimed primarily at integrating multiple data sources into each electronic record.

The nationally recognized interoperability standards for EHRs are currently endorsed by the Healthcare Information Technology Standards Panel (HTISP) and certified by the Certification Commission for Healthcare Information Technology (CCHIT). Those standards require EHRs to have the ability to communicate and exchange data accurately, effectively, securely, and consistently with different information technology systems, software applications, and networks in various settings such that the clinical or operational purpose and meaning of the data are preserved and unaltered as that data is exchanged. Thus, while an EMR is generally characterized as an electronic version of a physician's paper record, an EHR is characterized as a more comprehensive record containing additional data integrated to and from other sources. EHRs are further characterized as being either "basic" or "fully functional." A basic EHR includes patient demographics, problem lists, clinical notes, orders for prescription, and viewing laboratory and imaging results. A fully functional EHR includes patient demographics, problem lists, clinical notes, medical history and follow-up, orders for prescriptions, orders for tests, prescription orders sent electronically, laboratory and imaging results, warnings of drug interactions or contraindications, out-of-range test levels, and reminders for guideline-based interventions.

Most of the commercially available EMR and EHR systems, however, have not been well received by healthcare providers. In fact, according to a 2008 survey conducted by the National Center for Health Services (NCHS), a division of the Centers for Disease Control and Prevention (CDC), while about 40% of U.S. office-based physicians reported using EMR systems, only 17% reported using basic EHR systems, and only 4% reported using fully functional EHR systems. Part of the problem with traditional EHR systems is that many of the vendors of those systems have resisted making their software capable of exporting and importing patient information using uniform electronic messaging, document, and form management standards (e.g., the Health Level Seven (HL7) messaging standard, the Continuity of Care Document (CCD) document standard, and the Retrieve Form for Data Capture (RFD) form management standard).

At their core, EMR and EHR systems include large-capacity databases that contain patient information stored in structured, relational tables of searchable data. But, when that data is not captured and stored using uniform, standardized medical vocabularies and it is not transmitted using uniform messaging, document, and form management standards, it is of little use outside of the system in which the data is stored unless custom interfaces are designed to connect that system to other systems so that data can be shared therebetween. The process of developing different interfaces between the disparate formats used by different vendors is expensive and difficult. Moreover, the interfaces are also costly and labor-intensive to maintain.

The problem of interfacing different EHR systems is exacerbated by the fact that, in the present health care system, most patient visits are to small, self-contained practices that often treasure their autonomy and are unwilling and/or unable to acquire EHR systems unless each of those systems is individually tailored to the narrow objectives of each specific self-contained practice. Accordingly, most EHR vendors have been forced to provide healthcare providers with individually customized systems that employ stand-alone features and functions on the basis of what a specific practice group wants and needs. Accordingly, similar practice groups in adjacent counties may have very different system features and functions based on their different priorities. Thus, the various existing systems are not well suited for interaction and data exchange with each other, or for maintaining information that would be useful to the other systems, and the data collected by the different practice groups using EHR systems is therefore severely fragmented.

In addition, the enactment of the privacy and security regulations of the Health Insurance Portability and Accountability Act (HIPAA) has caused major changes in the way physicians and medical centers operate. Implementation of those regulations increased the overall amount of paperwork and the overall costs required for healthcare providers to operate. And, the complex legal implications associated with those regulations have caused concerns with compliance among healthcare providers. With regard to researchers, the HIPAA regulations have hindered their ability to perform retrospective, chart-based research as well as their ability to prospectively evaluate patients by contacting them for follow-up surveys. The HIPAA regulations have also led to significant decreases in patient accrual, increases in time spent recruiting patients, and increases in mean recruitment costs for researchers. And, by requiring that informed consent forms for research studies include extensive detail on how the participant's protected information will be kept private, those already complex documents have become even less user-friendly.

Because most EHR systems are not capable of exporting and importing patient information in a standardized format and do not utilize functions and features suited for interaction and data exchange with other systems, the fragmented pools of data collected using those systems cannot easily be combined with the ocean of data collected across a population of patients, much less a community of patients. Accordingly, collecting data across a broad swath of patients to perform medical research, to maintain disease registries, to track patient care for quality and safety initiatives, and to perform composite clinical and financial analytics remains a time-consuming and expensive process. For example, a clinical research organization (CRO) tasked with identifying patients that satisfy certain criteria for participating in a clinical trial must still sort through voluminous libraries of paper medical records and unstructured data, spending large amounts of time and money searching for candidates. Those problems have only been exacerbated by the regulations of HIPAA. Accordingly, there is a need for a system and method of using a plurality of integrated EHR systems to systematically analyze, collect, and track patient information across a vast patient population (e.g., a community, region, state, nation, etc.) while complying with HIPAA regulations in a more user-friendly manner In addition, there is a need for a system and method that utilizes that data to more effectively and efficiently perform clinical research, maintain disease registries, track patient care for quality and safety initiatives, and perform composite clinical and financial analytics.

SUMMARY OF THE INVENTION

Accordingly, to solve at least the above problems and/or disadvantages and to provide at least the advantages described below, a non-limiting object of the present invention is to provide a system and method of for analyzing, collecting, and tracking patient data across a vast patient population comprising a plurality of Electronic Health Record (EHR) systems provided at a plurality of healthcare provider sites, each EHR system comprising at least one means for capturing data for a plurality of patients in real time; comprising at least one research system for generating a dataset by performing at least one of analyzing, collecting, and tracking the data captured by the plurality of EHR systems in real time as the data is captured or from a database on which the captured data is stored; and comprising at least one workstation for setting the criteria by which the research system analyzes, collects and tracks the data captured by the plurality of EHR systems and for viewing the dataset generated by the at least one research system, wherein the dataset includes the data that corresponds to each of the criteria set at the workstation.

Those and other objects of the invention, as well as many of the intended advantages thereof, will become more readily apparent when reference is made to the following description, taken in conjunction with the accompanying drawings.

DETAILED DESCRIPTION OF THE EXEMPLARY EMBODIMENTS

Figure 1:
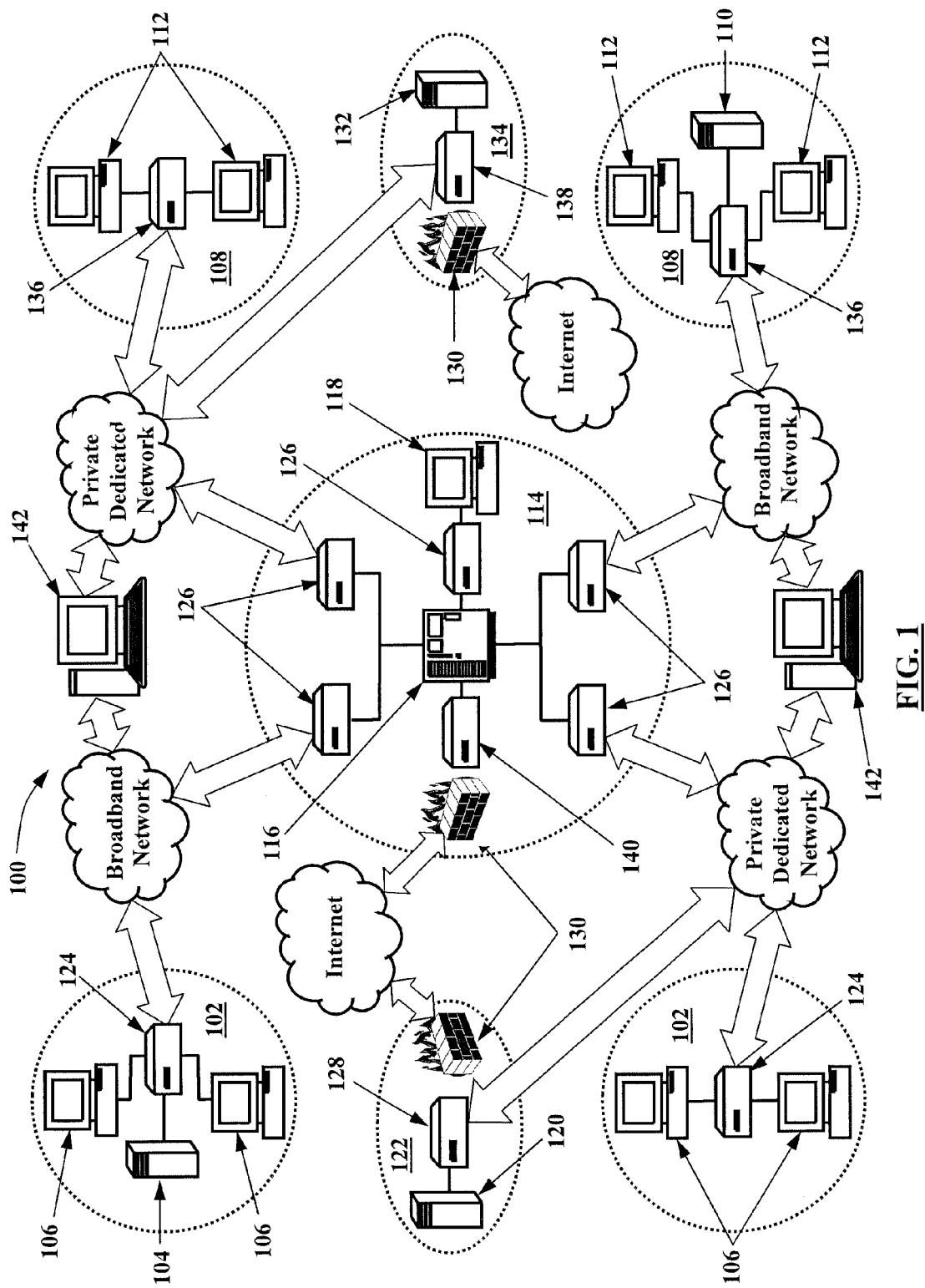
FIG. 1 illustrates the infrastructure of an integrated physician's network according to a non-limiting embodiment of the present invention.

Reference will now be made in detail to non-limiting embodiments of the present invention by way of reference to the accompanying drawings, wherein like reference numerals refer to like parts, components and structures.

The present invention provides infrastructure and functionality for analyzing, collecting, and tracking data across a vast patient population. And, the present invention provides infrastructure and functionality for utilizing that data to more effectively and efficiently perform medical research, maintain disease registries, track patient care for quality and safety initiatives, and perform composite clinical and financial analytics. The present invention may be implemented via an integrated physician's infrastructure (IPI) 100 that includes a network of fully functional EHR systems that are built on the same architecture, such as Greenway Medical Technologies, Inc.'s IPI that includes its PRIMESUITE brand EHR systems. The IPI 100 also includes a plurality of research systems built on the same architecture as the EHR systems so data can be shared seamlessly therebetween based on integration rather than interfacing different systems together.

By integrating the infrastructure and architecture of the various systems of the IPI 100, the present invention provides a single-vendor solution that allows for single-vendor support and the seamless sharing of standardized data across all of those systems. Accordingly, that data can be actively analyzed, collected, and tracked across a vast patient population in real time based on triggering events rather than requiring that queries be run on passive, "stale" data housed in a data repository. Moreover, by standardizing the format in which the data is captured and stored as well as the format by which it is exchanged across all of the systems of the IPI 100, the need for "middleware" type architecture to interface the various systems is eliminated. Thus, errors, duplication, and inconsistencies in data are also eliminated by the present invention. And, by building all of the systems of the IPI 100 on the same architecture, each system can be upgraded as a single entity with consideration for all functionality that may be affected.

Turning to the drawings, FIG. 1 illustrates an exemplary non-limiting embodiment of the infrastructure of the IPI 100 of the present invention. The IPI 100 is a network of computer systems comprising a plurality of EHR systems, a plurality of research systems, and at least one IPI provider system that are interconnected via a plurality of secured connections. Each EHR system is provided at a healthcare provider's site 102 and includes at least one client server 104 and at least one client workstation 106. Each research system may be provided at a researcher's site 108 and includes at least one partner server 110 and at least one partner workstation 112. And, each IPI provider system may be provided at the IPI provider's site 114 and includes at least one enhanced services server 116 and at least one administrator workstation 118. The EHR systems, research systems, and IPI provider system are all built on the same architecture so that the various systems of the IPI 100 and the functionality of each of their applications may be seamlessly integrated across the entire IPI 100.

The client server 104 of each EHR system contains all of the system applications and controls the operation of the EHR system. The client server 104 also controls communications with the other components of the IPI 100 and locally stores data collected using the EHR system. The client server 104 is at the center of the EHR system and may be located at a central location at a healthcare provider's site 102 for communication with each of the client workstations 106. In the alternative, as opposed to being hosted at the healthcare provider's site 102, all of the applications, controls, and data for the EHR system may be remotely hosted at a client server 120 located at a client data center 122. A client server 120 located at a client data center 122 may also host the applications, controls, and data for other EHR systems utilized by different healthcare providers.

The client workstations 106 provide a point of communication between healthcare providers and the client server 104 of the EHR system. The client workstations 106 of each EHR system may be provided at various locations, remote from the client server 104, throughout the healthcare provider's site 102 (e.g., in different physicians' offices). When the client server 104 is also located at the healthcare provider's site 102, the client workstations 106 communicate with the client server 104 and with each other over a Local Area Network (LAN) via a client router 124. The client server 104 and client workstations 106 of each EHR system also communicate with the enhanced services server 116 and administrator workstation 118 of the IPI provider system via a provider router 126 provided at the IPI provider's site 114, which preferably communicates with the client router 124 via a broadband network, such as DSL ("Digital Subscriber Line"), cable modem, or other high-speed connection.

When the client server 120 is provided at the client data center 122, the client workstations 106 communicate with that client server 120 via a client data center router 128 at the client data center 122 that preferably communicates with the client router 124 via a private dedicated network, such as a frame relay network. In that configuration, the client server 120 at the client data center 122 and the client workstations 106 at the healthcare provider's site 102 may also communicate with the enhanced services server 116 and administrator workstation 118 of the IPI provider system via the provider router 126 provided at the IPI provider's site 114, which communicates both with the client router 124 and the client data center router 128 via the private dedicated network. The client data center router 128 is located behind a firewall 130 to provide security from unauthorized internet access. And, use of a private dedicated network to facilitate the transmission of data when the client server 120 is provided at a location remote from the location of the client workstations 106 causes those components to perform like a private dedicated network and provides additional security to that network. Although the exemplary embodiment illustrated in FIG. 1 utilizes a broadband network when the client server 104 is provided at the healthcare provider's site 102 and a private dedicated network when the client server 120 is provided at the client data center 122, either a broadband network or a private dedicated network may be utilized in either configuration.

The partner server 110 of each research system contains all of the system applications and controls the operation of the research system. The partner server 110 also controls communications with the other components of the IPI 100 and locally stores data collected using the research system. The partner server 110 is at the center of the research system and may be located at a central location at a researcher's site 108 for communication with each of the partner workstations 112. In the alternative, as opposed to being hosted at the researcher's site 108, all of the applications, controls, and data for the research system may be remotely hosted at a partner server 132 located at a partner data center 134. A partner server 132 located at a partner data center 134 may also host the applications, controls, and data for other research systems utilized by different healthcare providers.

The partner workstations 112 provide a point of communication between researchers and the partner server 110 of the research system. The partner workstations 112 of each research system may be provided at various locations, remote from the partner server 110, throughout the researcher's site 108 (e.g., in different researchers' offices). When the partner server 110 is also located at the researcher's site 108, the partner workstations 112 communicate with the partner server 110 and with each other over a LAN via a partner router 136. The partner server 110 and partner workstations 112 of each research system also communicate with the enhanced services server 116 and administrator workstation 118 of the IPI provider system via the provider router 126 provided at the IPI provider's site 114, which preferably communicates with the partner router 136 via a broadband network.

When the partner server 132 is provided at the partner data center 134, the partner workstations 112 communicate with that partner server 132 via a partner data center router 138 at the partner data center 134 that preferably communicates with the partner router 136 via a private dedicated network. In that configuration, the partner server 132 at the partner data center 134 and the partner workstations 112 at the researcher's site 108 may also communicate with the enhanced services server 116 and administrator workstation 118 of the IPI provider system via the provider router 126 provided at the IPI provider's site 114, which communicates both with the partner router 136 and the partner data center router 138 via the private dedicated network. The partner data center router 138 is located behind a firewall 130 to provide security from unauthorized interne access. And, as discussed above, use of a private dedicated network to facilitate the transmission of data when the partner server 132 is provided at a location remote from the location of the partner workstations 112 causes those components to perform like a private dedicated network and provides additional security to that network. Although the exemplary embodiment illustrated in FIG. 1 utilizes a broadband network when the partner server 110 is provided at the researcher's site 108 and a private dedicated network when the partner server 132 is provided at the partner data center 134, either a broadband network or a private dedicated network may be utilized in either configuration.

The enhanced services server 116 of the IPI provider system contains all of the system applications used by the IPI provider to control and maintain the operation of the various systems of the IPI 100. The enhanced services server 116 also controls communications with systems outside of the IPI 100 and stores data aggregated from the various systems of the IPI 100. The enhanced services server 116 is provided at the center of the IPI 100 and can therefore serve as a centralized repository for the data aggregated from the various systems of the IPI 100. Access to that repository of data is controlled by the enhanced services server 116.

The administrator workstation 118 provides a point of communication between IPI administrators and the enhanced services server 116 and other systems within the IPI 100. The administrator workstation 118 may be provided at a location remote from the enhanced services server 116 at the IPI provider's site 114. The administrator workstation 118 communicates with the enhanced services server 116 over a LAN via a provider router 126. The enhanced services server 116 and administrator workstation 118 also communicate with the client servers 104 and client workstations 106 of the EHR systems and the partner servers 110 and partner workstations 112 of the research systems via the provider routers 126 provided at the IPI provider's site 114. As discussed above, the provider routers 126 communicate with the client routers 124, the client data center routers 128, the partner routers 136, and the partner data center routers 138 of the EHR systems and research systems, respectively, via a broadband network and/or a private dedicated network. The enhanced services server 116 can control at least one internet router 140 that is used to provide the various systems of the IPI 100 access to the internet when the client server 104 or partner server 110 do not provide such access. The internet router 140 is located behind a firewall 130 to provide security from unauthorized internet access. Administrative functionality for the applications of each system in the IPI 100 can be handled through the administrator workstation 118.

The functionality provided at each workstation 106, 112, and 118 is implemented via a single technology platform, such as web technologies that include markup languages, programming interfaces and languages, and standards for document identification and display (e.g., HyperText Markup Language (HTML), Visual Basic Script (VBScript), Extensible Markup Language (XML), Scalable Vector Graphics (SVG), JAVASCRIPT brand language, Cascading Style Sheets (CSS), Document Object Model (DOM), Virtual Reality Modeling Language (VRML), UNIX brand language, etc.). Those web technologies are utilized to provide users of the systems of the IPI 100 with web-browser-type user interfaces for communicating with the systems of the IPI 100. Accordingly, those web technologies may be used to facilitate remote access to all of the applications and data maintained by the various servers 104, 110, and 116 of the IPI 100 within a highly secured environment and enable communication between clients, partners, and administrators. Thus, substantially any device capable of employing those web technologies can be utilized as a workstation 106, 112, and 118 (e.g., a personal computer (PC), a laptop, a Personal Digital Assistant (PDA), a Secure Mobile Environment Portable Electronic Device (SME PED), etc.).

The functionality of each server 104, 110, 116, 120, and 132 of the IPI 100 is implemented via a central processor that manages the launching of script files and controls the operation of each server. Each central processor utilizes a central service utility that runs in the background and automates tasks within each system and across all of the systems of the IPI 100. Thus, the central service utility includes two types of utilities, one that runs on the individual servers 104, 110, 116, 120, and 132 of the respective systems and one that runs across all of the servers 104, 110, 116, 120, and 132 of the IPI 100.

The central service utility utilizes an event-driven design to perform tasks by monitoring a set of directories on the various servers 104, 110, 116, 120, and 132 of the IPI 100 and identifying the presence of an event or flag file before initiating, or triggering, an associated script or application. Multiple scripts and flags can be used together to complete tasks, and each task may consist of multiple scripts and/or third party programs. An event may include an empty file, a file comprising a single line of data, or a complete data file; and a flag file contains data that indicates what task is to be performed based on the event.

The central service utility supports tasks performed by standard internet-based services (e.g., Internet Information Services (IIS) and Active Server Page Network (ASP.NET) services) and standard software-framework-based services (e.g., Component Object Model Plus (COM+) and .NET services). The internet-based services provide functionality for the robust, interactive data exchange processes of the present invention, and provide functionality for presenting data to users of the various systems of the IPI 100 in a web-browser-type format. The software-framework-based services provide functionality for centrally managing all of the business logic and routines utilized by the present invention.

Each of the servers 104, 110, 116, 120, and 132 of the IPI 100 also include functionality for managing a relational database. Each database utilizes relational technology (e.g., a Relational Database Management System (RDBMS)) to manage all discrete data centrally, which facilitates the seamless sharing of information across all applications within each system of the IPI 100. And, by using standardized medical vocabularies to normalize data within each system of the IPI 100, information can also be shared seamlessly across the various systems of the IPI 100. That functionality reduces the potential for redundant data entry and data storage at the client server 104, 120 and partner server 110, 132 as that data is captured, and at the provider server 116 as that data is aggregated from the other servers. In addition, by storing data in relational databases, that data can be more efficiently queried to produce de-identified data sets.

To further facilitate the efficient querying of data, each database also utilizes standardized database languages designed for the retrieval and management of data in relational database, such as the Structured Query Language (SQL) and XML-Related Specifications (e.g., SQL/XML). Those standardized database languages are used to assign normalized extensions to particular types of data so that data can be more easily located within a database. And, in addition to standard extensions provided as part of those languages, those languages can also be used to define proprietary extensions unique to the system in which they are employed. Accordingly, the present invention provides functionality for storing data in a meaningful way that provides fast, easy access by any system in the IPI 100, which further enhances the data querying capabilities of the present invention.

In a preferred embodiment, the functionality provided at each workstation 106, 112, and 118 and each server 104, 110, 116, 120, and 132 of the IPI 100 is implemented using a tiered architecture. For example, the functionality of the workstations 106, 112, and 118 may be implemented in a user tier; the functionality of the central service utility of the servers 104, 110, 116, 120, and 132 may be implemented in a business tier; and the functionality of the databases of the servers 104, 110, 116, 120, and 132 may be implemented in a data tier. Accordingly, both a data tier and a business tier are located on each server 104, 110, 116, 120, and 132, while a client tier is located on each workstation 106, 112, and 118. In that configuration, the business tier is the middle tier and utilizes its standard internet-based services and standard software-framework-based services to analyze, collect, and track the data in the data tier and present it to a user of the IPI 100 at the user tier. The business tier may access the data in the data tier using a set of computer software components provided as part of the software-framework-based services (e.g., ADO.NET), and may transmit that data to the client tier using application-level protocol for the internet-based services (e.g., Hypertext Transfer Protocol Secure (HTTPS)).

That architecture may be based on Microsoft Corporation's Distributed Internet Applications (DNA) architecture, which uses .NET objects and Web Services for business rules and COM+ for resilient database storage and retrieval. Using the DNA architecture, the user tier would utilize Microsoft Corporation's Smart Client software as the client platform; the business tier would be implemented on Microsoft Corporations WINDOWS 2008 brand server using IIS, ASP.NET, Microsoft Corporation's Component Service, and .NET middle-tier objects; and the data tier would implement Microsoft Corporation's SQL*Server. Such a standard n-tier design model provides separation of the detailed business rules from the data storage functionality at the data tier and data presentation functionality at the user tier. In the present invention, such architecture also provides for tighter integration of the functionality within each system of the IPI 100.

In addition, the integrated architecture of the present invention enables a single source of support to minimize the cost of ongoing system maintenance and provides a scalable solution that allows the various systems of the IPI 100 to be expanded or contracted for large healthcare communities or specific healthcare specialties, respectively. Moreover, providing a single-vendor solution on a single technology platform in that manner allows the IPI provider to push new or updated system software to all of the systems in the IPI 100 simultaneously whenever that software is replaced or revised, thus ensuring seamless data exchange across all of those systems.

To further facilitate the seamless exchange of data across all of those systems, each of the various systems of the IPI 100 may utilize a controlled medical vocabulary, such as the Systematized Nomenclature of Medicine, Clinical Terms (SNOMED CT). SNOMED CT is a scientifically validated collection of well-formed, machine-readable, and multi-lingual healthcare terminology that provides a standardized nomenclature for use in capturing, indexing, sharing, and aggregating healthcare data across specialties and sites of care. Because the common language employed by SNOMED CT reduces the variability in the way data is captured, encoded, and used, it is particularly suited for use in electronic medical records, ICU monitoring, clinical decision support, medical research studies, clinical trials, computerized physician order entry, disease surveillance, image indexing, and consumer health information services. SNOMED CT is currently maintained by the International Health Terminology Standards Development Organization (IHTSDO).

The present invention also utilizes other standardized medical terminologies and classification systems, such as the International Classification of Diseases (ICD), RxNorm, Logical Observation Identifiers Names and Codes (LOINC), and Current Procedural Terminology (CPT). ICD is a coded classification system for identifying the signs, symptoms, abnormal findings, complaints, social circumstances, and external causes of various injuries and diseases, and it is currently maintained jointly by the National Center for Health Statistics (NCHS) and the Centers for Medicare & Medicaid Services (CMS). RxNorm is a coded classification system for identifying clinical drugs and doses administered to patients, and it is currently maintained by the National Library of Medicine (NLM). LOINC is a coded classification system for identifying laboratory and clinical observations, and it is currently maintained by the Regenstrief Institute, Inc. And, CPT is a coded classification system for describing medical, surgical, and diagnostic procedures, and it is currently maintained by the American Medical Association (AMA). By using those standardized nomenclatures, the present invention avoids duplicate data capture while facilitating enhanced health reporting, billing, and statistical analysis. And, by mapping each of those standardized nomenclatures to the SNOMED CT vocabulary, duplicate data capture is further avoided while providing a framework for managing different language dialects, clinically relevant subsets, qualifiers and extensions, as well as concepts and terms unique to particular organizations or localities.

The present invention maintains each of those standardized nomenclatures across all of the systems of the IPI 100 in an extensive "back-end" repository so that they can not only be mapped to data captured by those systems, but can also be mapped to other widely accepted coded classification systems to further improve the functionality of the present invention. For example, ICD codes can be mapped to associated CPT codes for claims processing, CPT codes can be mapped to result codes from various laboratories to facilitate lab interactions, and RxNorm codes can be mapped to First DataBank, Inc.'s NATIONAL DRUG DATA FILE PLUS (NDDF PLUS) brand coded classification system to facilitate pharmacy management and drug interaction analysis. In addition to normalizing data throughout the IPI 100 to eliminate duplicate data capture and to streamline the sharing of data, the use of all of the standardized nomenclatures described herein also allows the various systems of the IPI 100 to more easily mediate inbound and outbound data communications with external information systems 142 outside of the IPI 100. External information systems 142 include, but are not limited to, external EHR systems, external research systems, disease registry systems, public health organization systems, safety/quality organization systems, and claims processing systems.

When the systems of the IPI 100 must interface with external information systems 142 to facilitate the exchange of data in real time, the present invention includes an interoperability engine to facilitate integration with such external information systems 142. The interoperability engine supports various standardized formats as well as various vendor-specific delimited files and fixed width files. Thus, instead of relying on distributed interfaces to various applications, the present invention provides a single platform maintained on the secure, managed network infrastructure of the IPI 100, thereby extending the seamless exchange of data across the various systems of the IPI 100 to include external information systems 142.

For example, the interoperability engine supports a uniform messaging standard, such as the Health Level Seven (HL7) messaging standard, for identifying triggering events and the associated data that is to be exchanged based on the triggering event. In the present invention, a triggering event includes an event at a client's site 102 or a partner's site 108 that creates the need for data to flow among systems, such as registering a new patient at a client's site 102 or submitting available clinical trials at a partner's site 108. Among the external information systems 142 that can be interfaced in real time using the HL7 messaging standard are EHR systems that include diagnostic equipment for capturing data at the point of care. Accordingly, the systems of the IPI 100 can exchange information such as patient demographics, processing pre-certifications, orders, results, labs, and prescriptions with external information systems 142 in real time based on triggering events. The HL7 messaging standard is utilized by most healthcare information systems, such as the hospital information systems provided by McKesson HBOC Inc., Meditech Inc., and Cerner Corp. The contents of the HL7 messaging standard are hereby incorporated by reference.

In addition to supporting a uniform messaging standard for the real-time exchange of data with external information systems 142, the interoperability engine of the present invention also supports a uniform document standard, such as the Continuity of Care Document (CCD) standard, for specifying the structure and semantics of electronic documents in which data is captured. The CCD standard is a structured Extensible Markup Language (XML) standard developed by HL7 and the American Society for Testing and Materials (ASTM) to harmonize the data format between HL7's Clinical Document Architecture (CDA) standard and ASTM's Continuity of Care Record (CCR) standard. The CDA standard provides an exchange model for clinical documents (e.g., discharge summaries and progress notes) that uses various coded vocabularies (i.e., the coded vocabularies discussed above, such as ICD, etc.) to assign both computer-readable structured components and human-readable textual components to electronic documents so those documents can be easily parsed and processed electronically and retrieved, read, and understood by the people who use them. And, the CCR standard provides patient health summary model for clinical documents by identifying the most relevant and timely core health-related information about a patient so that information can be sent electronically from one healthcare provider to another. Thus, the CCD adds content to the exchange model of the CDA by using the summary model of the CCR to identify the various sections of the clinical document that collectively represent a "snapshot" of a patient's information, such as the patient's demographics, insurance information, diagnosis, problem list, medications, allergies, and care plan. Accordingly, the CCD standard supports more streamlined exchanges with and between EHR systems than supported by the CDA and CCR standards alone. The contents of the CCD standard are hereby incorporated by reference.

Supported by the CCD document standard, the interoperability engine of the present invention also supports a uniform form management standard, such as the Retrieve Form for Data Capture (RFD) form management standard, to facilitate the retrieval, completion, and submission of forms between the systems of the IPI 100 and with external information systems 142. The RFD standard was developed through a joint effort between the Integrating the Healthcare Enterprise (IHE) and Clinical Data Interchange Standards Consortium (CDISC) organizations to advance public health by providing a standardized means for retrieving and submitting forms data between researchers and healthcare providers and electronic data capture systems and other data collection agencies. The RFD standard makes medical research and healthcare more efficient by providing a method for capturing data within a user's current application in a manner that meets the requirements of an external system. The RFD standard supports the retrieval of forms from a Form Manager, display and completion of a form by a Form Filler, and return of instance data from the display application to a Form Receiver and a Form Archiver.

A Form Manager is responsible for providing the desired form, such as the Food and Drug Administration (FDA). A Form Filler is responsible for inputting data into the form, such as the user of an EHR system. A Form Receiver is responsible for receiving the primary data input by the Form Filler for processing purposes. And, a Form Archiver is responsible for receiving the data input from the Form Filler for archival purposes. The Form Receiver and Form Archiver may or may not be the same entity as each other, the Form Manager, or the Form Filler. The contents of the RFD standard are hereby incorporated by reference.

In addition to facilitating integration with external information systems 142, the CCD document standard and RFD form management standard can also be utilized within each system of the IPI 100 to facilitate the seamless exchange of data between those internal systems. Thus, the present invention provides a computer-based production environment that utilizes the CCD document standard and RFD form management standard to collect patient information in real time at the point of care using a plurality of EHR systems, both those that are part of the IPI 100 and those that are external to the IPI 100. Moreover, by facilitating the integration of external information systems 142 with the systems of the IPI 100 using the standardized formats supported by the interoperability engine, the present invention provides functionality for a researcher to collect medical data across an even larger patient population than that covered by various systems of the IPI 100.

In addition, utilizing those standardized medical terminologies and classification systems facilitates both systematic and data-level integration across each of the systems of the IPI 100 such that the research functionality of the research systems is seamlessly integrated into the workflows of the EHR systems, which eliminates duplicate data entries between the EHR systems and the electronic source documentation of the research systems. And, because the IPI 100 of the present invention includes a network of EHR systems that are built on the same architecture as the research systems, that research functionality can be employed seamlessly across the entire IPI 100 to simultaneously collect data from all of the EHR systems and electronically transfer the collected data to the research systems, which benefits all stakeholders by decreasing the input time and increasing the accuracy of data. Moreover, by providing an interoperability engine that integrates those systems with external information systems 142, the research functionality of the present invention can also be employed seamlessly across external research systems 142 to exchange data with external EHR systems and external research systems. Accordingly, that data can easily be exchanged with data from other clinicians, research institutes, universities, and pharmaceutical companies for broad-based ongoing research and can be used by researchers, scientists, and physicians to better understand and combat health issues and diseases.

Each system of the IPI 100 also includes features that address all of the security, privacy, and transactional regulations of the Health Insurance Portability and Accountability Act (HIPAA). To address HIPAA's security regulations, each system of the IPI 100 may include biometric login; restricted access based on login authorization (e.g., restricting access to only individual charts or chart sections); routine and event-based audits to identify potential security violations (e.g., identify who looked at what section of a chart and when); and restricted ability to copy, print, fax, e-mail, and export information based on login authority. To address HIPAA's privacy regulations, each system of the IPI 100 may include functionality for consent tracking and disclosure logging, functionality for de-identifying data, and functionality for automatically populating consent forms with the extensive details required by HIPAA explaining how a participant's protected information will be kept private. And, to address HIPAA's transactional regulations, each system of the IPI 100 may utilize Electronic Data Interchange (EDI) standards to structure the electronic transfer of claim billing information between the systems of the IPI 100 and external information systems 142, such as a claims processing system. The contents of HIPAA are hereby incorporated by reference.

By providing automated compliance with many of the requirements of HIPAA, the present invention helps resolve many of the intricacies of HIPAA, which alleviates much of the concern healthcare providers have had with the complex legalities and potentially stiff penalties associated with HIPAA. In addition, by providing a system that streamlines and automates the electronic capture and flow of data between healthcare providers in a secured manner, the present invention also eliminates much of the additional paperwork and labor associated with HIPAA, which reduces the amount of cost, time, and physical space required of healthcare providers to comply with HIPAA. And, by providing a single-vendor IPI 100 comprising a large number of integrated EHR systems and research systems, the present invention provides access to data for a vast patient population that can be used in clinical trials, disease registries, evidence-based medical and pharmaceutical research, and clinical and financial statistical analysis. Accordingly, the present invention makes it easier for researchers to recruit patients for research by reducing the time and costs associated with recruiting those patients, which not only overcomes many of the research related problems associated with existing paper-based processes and the regulations of HIPAA, but also provides a mechanism for healthcare providers to increase revenue and foster the ongoing improvement in quality of care for patients through their participation in the research facilitated by the present invention.

By way of further non-limiting example, the research functionality of the present invention may be used to quickly and accurately locate a large number of patients for participating in a clinical trial by running a sequential filtering process across the systems of the IPI 100. By utilizing an IPI 100 that includes a large network of EHR systems built on the same architecture, the filtering process can be run quickly and accurately across the databases on each client server 106 and/or querying a central database on the enhanced services server 116. And, where the IPI 100 is employed on a national scale, the results of that filtering process provide a larger pool of patients, and therefore a more desirable cross-section of people, from which researchers can recruit participants for clinical trials. For example, utilizing the present invention over Greenway Medical Technologies, Inc.'s IPI will currently provide researchers access to data for more than fourteen million active patients collected at more than eight hundred sixty healthcare provider sites across at least forty-seven U.S. states. Collecting, tracking, and analyzing data on such an expansive scale is indicative of the present invention's functionality.

Thus, a clinical trial sponsor, such as a pharmaceutical company, can utilize the present invention to quickly and accurately identify and register patients that qualify for clinical trials. The clinical trial sponsor can become a partner with the IPI provider and utilize the functionality of the present invention to locate patients within the IPI 100 network that qualify for a clinical trial, or the clinical trial sponsor can solicit proposed clinical trials through Clinical Research Organizations (CROs) who will become partners of the IPI provider and utilize the functionality of the present invention to locate patients within the IPI 100 network that qualify for a proposed clinical trial. To utilize that functionality, the clinical trial sponsor or CRO will develop specific clinical criteria that patients must satisfy to qualify for participation in the clinical trial. Those criteria are given to the IPI provider, who utilizes the present invention to run a sequential filtering process 300 and determine the number of patients within the network of the IPI 100 that qualify for the clinical trial. In the alternative, the clinical trial sponsor or CRO may utilize the present invention to run the sequential filtering process. But, before a clinical trial sponsor or CRO obtains access to the network of the IPI 100 and/or the data captured thereon, the clinical trial sponsor or CRO must register as a research partner of the IPI provider and agree to certain provisions to ensure compliance with HIPAA's regulations.

Figure 2:
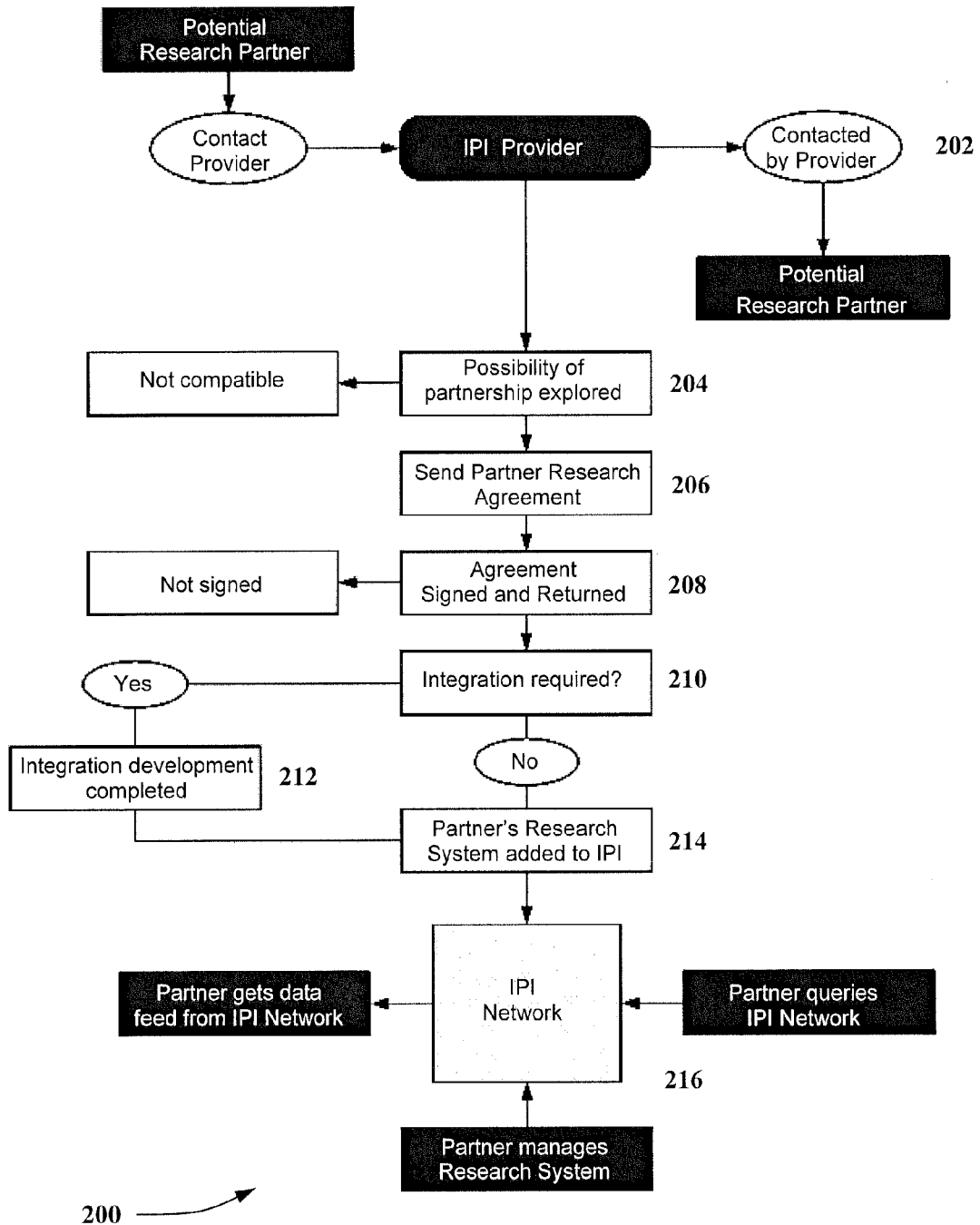
FIG. 2 is a schematic block diagram illustrating the functional steps of a sequential filtering process according to a non-limiting embodiment of the present invention.

As FIG. 2 illustrates, the partner registration process 200 includes several steps before a potential research partner can utilize the functionality of the present invention. At step 202 of the partner registration process 200, a potential research partner can contact the IPI provider or the IPI provider can contact the potential research partner via any suitable means, such as via a link on the IPI provider's internet home page or via an e-mail. At step 204 of the partner registration process 200, the IPI provider and the potential research partner explore the possibility of the partnership and determine whether the two entities are compatible with each other for performing the desired research. If the IPI provider and the potential research partner agree that they are compatible, the IPI provider sends a Partner Research Agreement to the potential research partner at step 206 of the partner registration process 200.

The IPI provider and the potential research partner may negotiate the terms of the Partner Research Agreement, except for those requiring compliance with the regulations of HIPAA and other state and federal laws. For example, the IPI provider and the potential research partner may negotiate the format and protocol by which data will be exchanged between the potential research partner's research system and external information systems 142 utilized by the potential research partner, such as a Clinical Trials Management Systems (CTMS) and/or Electronic Data Capture (EDC) systems. The Partner Research Agreement may also identify a CRO, such as eCast Corp. or Outcome Sciences Inc., who will provide a Clinical Research Coordinator (CRC) to conduct the clinical trial at the point of care. After all of the terms of the Partner Research Agreement are negotiated, the agreement is executed and returned to the IPI provider at step 208 of the partner registration process 200.

If the research partner negotiated for its research system to be developed to exchange data with any of the research partner's external information systems 142 in a format other than the standardized format in which that data is captured by the systems of the IPI 100, the interoperability engine is used to facilitate integration of those external information systems 142 with the research partner's research system at step 210 of the partner registration process 200. After integration development is completed at step 212 of the partner registration process 200, or if no integration was required, the partner's research system is added to the network of the IPI 100 at step 214 of the partner registration process 200. After the research partner's research system is added to the network of the IPI 100, the research partner is given access to a research partner web portal at step 216 of the partner registration process 200 through which the research partner can manage its research system, set up data feeds, and run queries. Managing its research system includes viewing those research tasks the research partner is in charge of completing, and setting up data feeds and running queries includes choosing the criteria by which de-identified data is collected, tracked, and analyzed by the research system.

Figure 3:
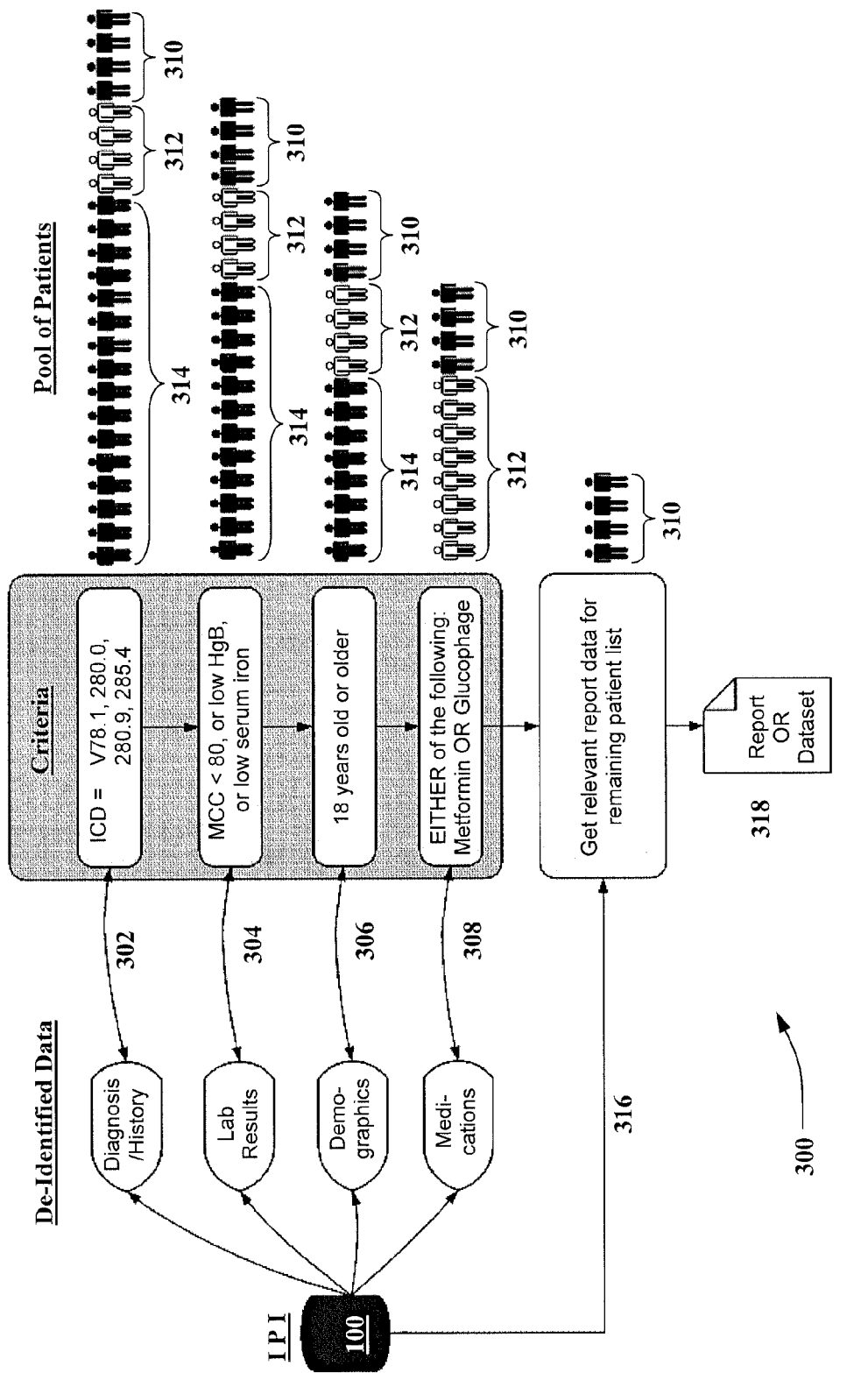
FIG. 3 is a schematic block diagram illustrating the functional steps of a partner registration process according to a non-limiting embodiment of the present invention.

As FIG. 3 illustrates, the research system may analyze, collect, and/or track data by applying a sequential filtering process 300 to generate de-identified data sets from the data captured by the various systems of the IPI 100. The sequential filtering process is performed by a codified search of a universal vocabulary common to all databases using the SQL language to compare lexicons and prepare the desired result. That search can be performed utilizing functions/procedures that can be integrated into the databases of the various systems of the IPI 100. Such functions include SQL functions and, for large and/or complex queries, Stored Procedures (SPs) and User Defined Functions (UDFs). Using those functions, data can be efficiently queried from the databases of the various servers 104, 110, 116, 120, and 132 of the IPI 100, either individually, simultaneously, or at a central database where data has been aggregated (e.g., the database on the enhanced services server 116).

In the example illustrated, the sequential filtering process includes steps 302-308 for determining the number of patients among a large pool of patients that qualify for a clinical trial 310 (hereinafter "qualifying patients 310"). Although FIG. 3 illustrates separate steps for performing the sequential filtering process, the research functionality of the present invention automatically performs those after a research partner chooses the criteria by which qualifying patients 310 are to be identified. According, a research partner need merely choose the criteria for identifying patients that qualify for a clinical trial via its research partner web portal, and the research functionality will automatically perform the sequential filtering process across the systems of the IPI 100 to determine the number of patients that satisfy all of those criteria.

In addition, although the pool of patients illustrated in FIG. 3 only includes twenty-four patients, that number of patients is provided for ease of explanation. As discussed above, the pool of patients can actually include fourteen million or more active patients. Among the pool of patients at each step, there may be patients that do not satisfy the associated criteria 312 and patients that do satisfy the associated criteria 314 in addition to the qualifying patients 310 that qualify for the clinical trial by satisfying the criteria at every step.

Step 302 in the exemplary sequential filtering process 300 includes querying de-identified patient diagnosis/medical history data and determining the number of patients with specific diagnoses. Those diagnoses are queried based on the ICD values captured for those patients (e.g.; V78.1, which corresponds to screening for other and unspecified deficiency anemia; 280.0, which corresponds to iron deficiency anemia secondary to blood loss (chronic); 280.9, which corresponds to iron deficiency anemia unspecified; and 285.1, which corresponds to acute posthemorrhagic anemia). Step 302 in the sequential filtering process 300 reveals that twenty of twenty-four patients have been diagnosed with at least one of the health conditions specified.

Step 304 in the exemplary sequential filtering process 300 includes querying de-identified patient lab results data and determining the number of the remaining twenty patients that have a mean corpuscular volume (MCV) less than eighty, low hemoglobin (HgB), or low serum iron. The patient lab results may be queried based on the associated LOINC classification. Because the filtering process is sequential, only the data for the twenty patients that satisfied the criteria at step 302 are queried at step 304. Step 304 in the sequential filtering process 300 reveals that sixteen of the twenty patients that have been diagnosed with at least one of the health conditions specified in step 302 also have the lab results specified in step 304.

Step 306 in the exemplary sequential filtering process 300 includes querying de-identified patient demographic data and determining the number of the remaining sixteen patients that are eighteen years old or older. The demographic data is de-identified in accordance with the HIPAA privacy regulations, so the only element of data that is queried is the year. Again, because the filtering process is sequential, only the sixteen patients that satisfied the criteria at step 302 and step 304 are queried at step 306. Step 306 in the sequential filtering process 300 reveals that twelve of the sixteen patients that have been diagnosed with at least one of the health conditions specified in step 302 and at least one of the lab results specified in step 304 also satisfy the demographic requirement specified in step 306.

Step 308 in the exemplary sequential filtering process 300 includes querying de-identified patient medication data and determining the number of the remaining twelve patients that have been prescribed either Metformin or GLUCOPHAGE brand Metformin The patient medication data may be queried based on its associated RxNorm classification. By querying only the twelve patients that satisfied the criteria at steps 302-306, step 308 in the sequential filtering process 300 reveals that four of the original twenty-four patients have been diagnosed with at least one of the health conditions specified in step 302, have at least one of the lab results specified in step 304, satisfy the demographic requirement specified in step 306, and have been prescribed one of the medications specified in step 308. Thus, the sequential filtering process 300 determines that there are four qualifying patients 310 that qualify for the clinical trial by satisfying each of the established criteria.

At step 316, any additional de-identified data that is relevant to the clinical trial is retrieved from the IPI 100 for qualifying patients 310. And, at step 318, all of the retrieved data for the qualifying patients 310 is presented in the form of an electronic report or a dataset. When the sequential filtering process 300 is initiated by the IPI provider at the IPI provider's site 114, the electronic report or dataset is presented to the IPI provider at an administrator workstation 118 and can be transferred to the research partner that requested it at a researcher's site 108 or a third party (e.g., a pharmaceutical company) at an external information system 138 via one of the secured connections of the IPI 100. And, when the sequential filtering process 300 is initiated by a research partner at the researcher's site 108 or is transferred from the IPI provider to the research partner at the researcher's site 108, the electronic report or dataset is presented to the research partner at a partner workstation 112. A research partner can transfer the electronic report or dataset from the research partner's research system to an external information system 142, such as a CTMS or EDC system, via one of the secured connections of the IPI 100. Regardless of who initiates the sequential filtering process via the research system, the research partner can establish the criteria for that search through its research partner web portal using its partner workstation 112, which, as discussed above, may include a PC, a laptop, a PDA, and an SME PED.

Thus, the present invention can utilize a sequential filtering process 300 to quickly and accurately generate an electronic report or dataset for patients that qualify for a clinical trial that can be easily disseminated to the parties requesting that data. Moreover, that data can be collected in a matter of minutes in lieu of the months it used to take to identify qualifying patients 310, which saves clinical trial sponsors and CROs millions of dollars. And, because the present invention provides an integrated system comprising standardized data for over fourteen million active patients, the patients that qualify for the clinical trial represent a more accurate cross-section of the population from which they are drawn, which is extremely desirable for clinical trials.

Although the sequential filtering process 300 illustrated in FIG. 3 is described with respect to locating patients that qualify for clinical trials, the present invention also provides similar research functionality for generating reports or datasets of other clinical and financial information across the vast network of the IPI 100. For example, the present invention can be used to analyze, collect, and track data for comparing a medical practice to other practices (e.g., in the same specialty, in the same region, of the same size, etc.) based on customized criteria (e.g., previous performance, specified financial goals, etc.) or national standards and benchmarks (e.g., Medical Group Management Association (MGMA) certifications, Agency for Healthcare Research and Quality (AHRQ) quality indicators, National Committee for Quality Assurance (NCQA) accreditations, Healthcare Effectiveness Data and Information Set (HEDIS) measures, CMS initiatives, etc.). The present invention performs analytics on those electronic reports or datasets to generate average values that can be easily compared by clients and research partners. Such comparisons provide healthcare providers with guidance for improving the clinical quality and financial performance of their respective practices.

The present invention also provides functionality similar to the sequential filtering process 300 illustrated in FIG. 3 for generating reports or datasets that track the effects of various drugs and medical procedures on patients within the network of the IPI 100. For example, a research partner, such as a pharmaceutical company, can utilize the present invention to identify any adverse effects of one of its drugs by tracking patients that have taken that drug, alone or in combination with other drugs, and determining whether any pattern of illnesses or side effects appears among those patients. And, because the IPI 100 of the present invention actively analyzes, collects, and tracks data in real time, drug companies can quickly and accurately identify any adverse events and respond by removing the drug from the market or altering the composition of the drug. Moreover, the present invention provides functionality that allows the IPI provider or a research partner to establish criteria for automatically identifying such adverse events as they occur.

In addition to tracking adverse events, the research functionality of the present invention can also be used to track the efficacy of various drugs by tracking actual usage of those drugs in various scenarios. That data can be used to verify and reinforce the conclusions drawn as a result of a clinical trial and confirm that marketing authorization of the drug was valid. Accordingly, the research functionality of the present invention can be utilized to accomplish any required pharmacovigilance (PV) activities during a drug's post-marketing period, such as those required by the World Health Organization (WHO) International Drug Monitoring Programme. For example, the present invention can be used to study how certain drugs are used and their impact on pregnancy outcomes by identifying pregnancy events across the systems of the IPI 100 and linking them to child births and deaths, birth defects, and the drugs administered to the pregnant patients based on the data captured for the pregnant patients at the various systems in the IPI 100.

The research functionality of the present invention can also be used to provide real-time feedback for various other purposes, such as tracking diseases for disease registries or even tracking the flu. Moreover, that type of data tracking can be performed by globally polling the data on the systems of the IPI 100 as a whole in lieu of querying that data to identify specific datasets. Utilizing that broader, global polling functionality in real time, the research functionality of the present invention can be used as an electronic biosurvielance system for providing early warnings of health threats, early detection of health events, and overall situational awareness of disease activity on a national scale. The research functionality achieves those objectives by monitoring the environment for bacteria, viruses, and other biological agents that cause disease in real time across all of the systems of the IPI 100.

Returning to the example of the present invention's functionality for identifying qualifying patients 310, the sequential filtering process 300 only identifies the number of patients that satisfy all of the criteria for a clinical trial and provides de-identified data for those patients. The query results do not include any patient-specific information. For a research partner to obtain access to patient-specific data from a particular user of the IPI 100, that user must establish a formal relationship with the IPI provider by becoming a research client of the IPI provider. Accordingly, the present invention also provides functionality for recruiting IPI users to become research clients of the IPI provider. When an IPI user becomes a research client of the IPI provider, the IPI user not only authorizes research partners of the IPI provider to access patient-specific data for the IPI user's patient population, the IPI user is also given access to the infrastructure within the IPI 100 that interconnects all of the systems of the IPI 100 to the IPI provider's research partners' research systems (hereinafter "the Research Network").

Figure 4:
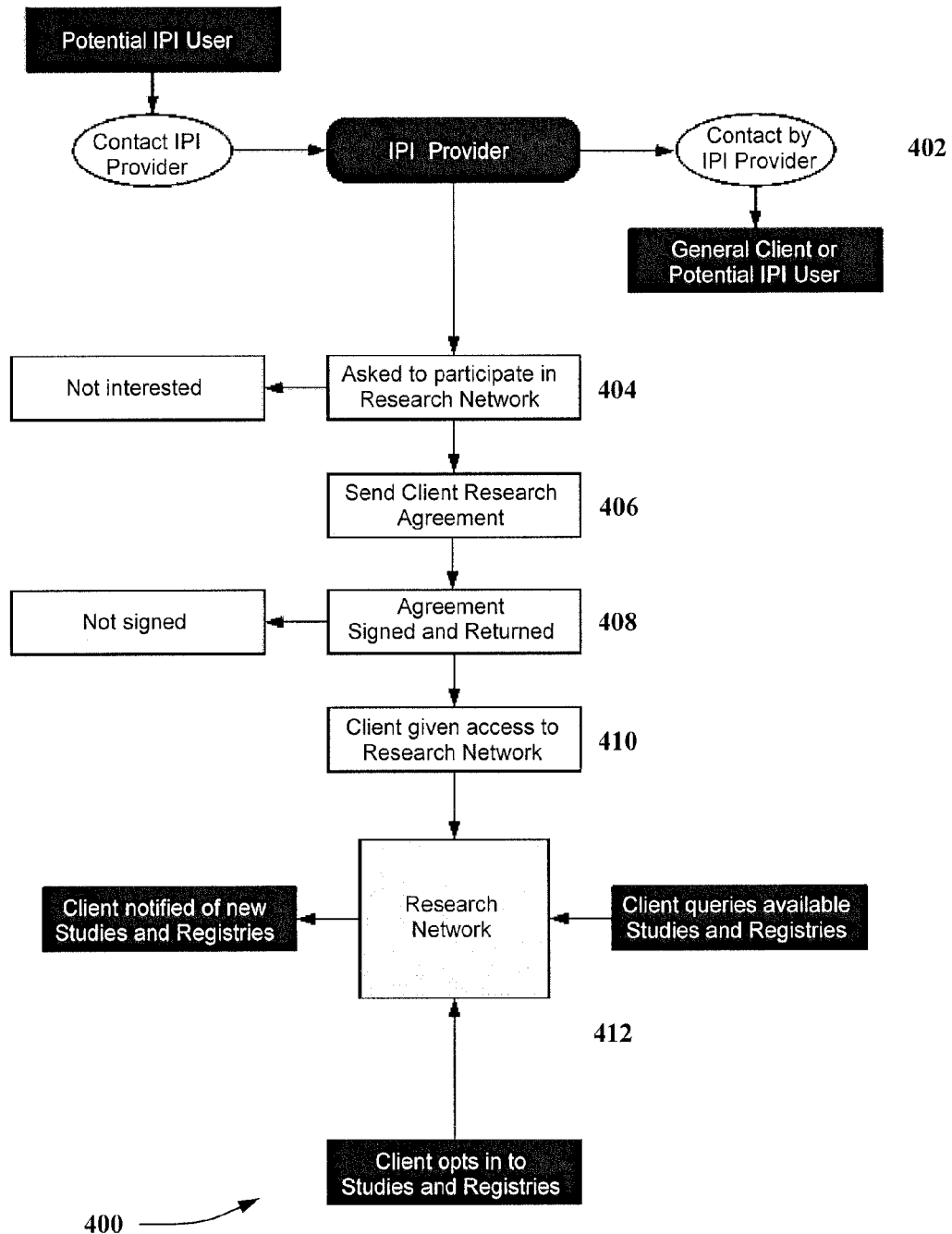
FIG. 4 is a schematic block diagram illustrating the functional steps of a client registration process according to a non-limiting embodiment of the present invention.

As FIG. 4 illustrates, the client registration process 400 includes several steps before an IPI user can access the Research Network of the present invention. At step 402 of the client registration process 400, a potential user of the IPI 100 may contact the IPI provider to become a general client of the IPI provider and obtain at least one of the services provided by the IPI provider (e.g., an EHR system). In the alternative, the IPI provider may solicit potential IPI users to obtain at least one of the services provided by the IPI provider or may contact existing general clients that have already obtained at least one of the services provided by the IPI provider. Once contact is made at step 402 of the client registration process, the potential IPI user or existing general client is asked if it would like to be a research client in addition to being a general client at step 404 of the registration clients. By becoming a research client in addition to a general client, an IPI user is able to participate in the Research Network of the present invention as part of the services provided to the user by the IPI provider. Accordingly, the present invention provides an effective means for recruiting healthcare providers to participate in its Research Network.

If the IPI user is interested in participating in the Research Network, a Client Research Agreement is sent to the IPI user at step 406 of the client registration process 400 via any suitable means, such as via e-mail or via a link in the web portal of the system the IPI user is utilizing to obtain the IPI provider's services. The terms of that agreement set out the requirements that will be adhered to by both parties to ensure compliance with the regulations of HIPAA and other state and federal laws. If the IPI user agrees to the terms of the Client Research Agreement, the agreement is executed and returned to the IPI provider at step 408 of the client registration process 400. Because the IPI user is already using the services of the IPI provider, the system that the IPI user is utilizing to obtain those services is already integrated into the network of the IPI 100, and no integration is required for the IPI user to become part of the Research Network.

After the IPI user has executed and returned the Client Research Agreement at step 408 of the client registration process 400, the research client is given access to the Research Network at step 410 of the client registration process 400. The research client can access the Research Network at step 412 of the client registration process 400 via a research client web portal. The research client web portal provides functionality for the research client to easily view all of the clinical trials for which any of its patient's qualify, the criteria for each of those trials, and all of the patients that qualify for those trials. The research client can configure the research client web portal to send automatic notifications of any new clinical trials for which its patients qualify. The research client can also request to opt in to any available clinical trial via the research client web portal.

Participation in a clinical trial can be a source of income for those research clients that opt in to such trials, which serves as an incentive for more IPI users to become research clients. The more IPI users that become part of the Research System, the more powerful of a research tool the Research System becomes. But, before a research client can begin participating in a clinical trial, the qualifying patients 310 may need to be screened and give their authorization to verify their eligibility for the clinical trial.

Figure 5:
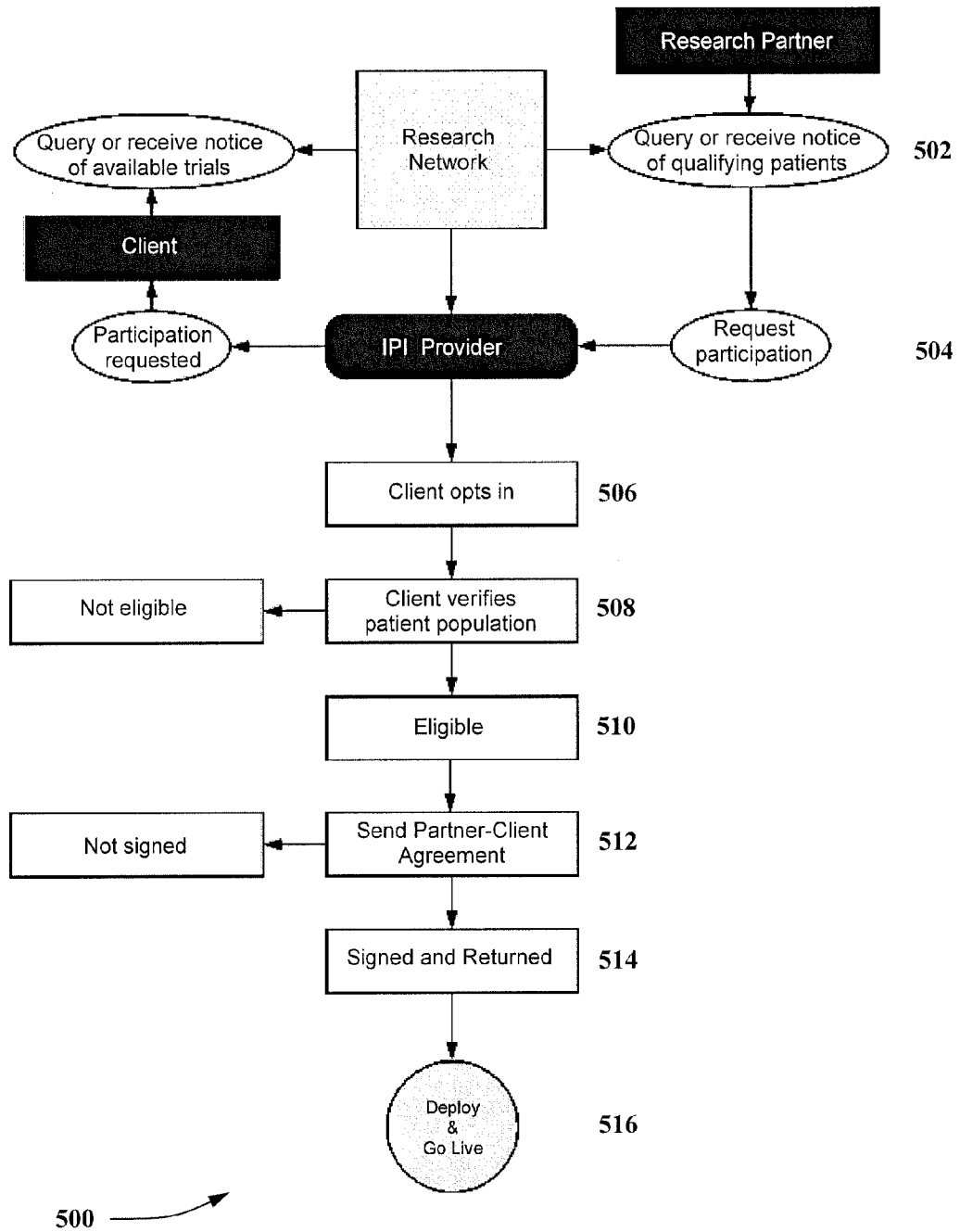
FIG. 5 is a schematic block diagram illustrating the functional steps of patient verification process according to a non-limiting embodiment of the present invention.

As FIG. 5 illustrates, the patient verification process 500 includes several steps before the research client becomes active in a clinical trial. At step 502 of the patient verification process 500, a research client can query or receive a notification from the Research Network of the available clinical trials for which the research client qualifies. Or, in the alternative, the research partner may query or receive a notification from the Research Network at step 502 of the patient verification process, identifying which research clients qualify for that research partner's clinical trial. Based on that query or notification, the research partner may contact the qualifying research client or the service IPI provider at step 504 of the verification process 500 to request that the qualifying research client participate in the research partner's clinical trial. Or, in yet another alternative, the IPI provider may automatically request that the qualifying research client participate in the research partner's clinical trial at step 504 of the verification process 500 based on its own query of the Research Network. Regardless of who generates the request for the qualifying research client to participate in the research partner's clinical trial, that request will go through the IPI provider so the IPI provider can facilitate verification of the qualifying patients 310 and execution of a Partner-Client Agreement between the research client and the research partner before the research client begins participating in the clinical trial via the IPI 100.

At step 506 of the verification process 500, the qualifying research client can opt in to the research partner's clinical trial based on the research client's query or notification at step 502 or based on the IPI provider's or research partner's request at step 504. After opting in to the clinical trial, the research client must verify its population of qualifying patients 310 at step 508 of the verification process 500. Verifying that a research client's qualifying patients 310 are eligible for the clinical trial may include a screening process by which the research client schedules follow-up visits (e.g., preemptory evaluations) with its qualifying patients 310 to run any other necessary tests to ensure that the qualifying patients 310 satisfy the requisite criteria for the clinical trial. Verifying that a research client's qualifying patients 310 are eligible for the clinical trial may also include having the qualifying patients 310 sign a consent form, pre-populated with the required HIPAA-mandated language regarding the patients' protected information, authorizing their physician to place each patient's information on the Research Network.

If a research client's qualifying patients 310 are verified as eligible to participate in the research partner's clinical trial at step 510 of the verification process 500, the IPI provider sends the research client and research partner a Partner-Client Agreement at step 508 of the verification process 500. The Partner-Client Agreement is between the research client and the research partner and sets forth all of the requirements and payments associated with performing the clinical trial. The Partner-Client Agreement also includes all language required to ensure both parties comply with the regulations of HIPAA. After both parties have executed the Partner-Client Agreement and returned it to the IPI provider at step 514 of the verification process 500, the research functionality of the present invention is deployed to the research partner and research client so they may go live and begin capturing clinical data in real time at the system of the IPI 100 utilized by the research client (e.g., an EHR systems).

As part of the research functionality deployed, the verified patients that are participating in the clinical trial are attached to the specific clinical trial so that the proper forms required for that clinical trial are automatically associated with and made available for those patients. In addition, triggering events are automatically associated with those forms according to the protocol established for the clinical trial so that the forms are made available only as certain events occur within the systems of the IPI 100. The manner in which the research functionality of the present invention can be used to complete and submit those forms is described in more detail below.

By simplifying and facilitating the interactions between research clients and research partners that are required to recruit research clients and get patients enrolled in clinical trials, the present invention provides for completing the enrollment process for a clinical trial in a matter of days instead of months. Accordingly, healthcare providers can quickly begin enrolling candidates, participating in the clinical trials, and receiving reimbursements form clinical trial sponsors or CROs via the functionality of the present invention. And, in addition to recruiting research clients and enrolling patients for clinical trials, similar methods can also be utilized for recruiting research clients and enrolling patients for other types of medical research, such as disease registries and quality of care initiatives. Thus, the functionality of the present invention eliminates many, if not all, of the hurdles put in place by HIPAA that otherwise deter healthcare providers from participating in medical research.

In addition to the present invention's functionality for recruiting research clients and enrolling patients to participate in medical research, the present invention also provides functionality for carrying out that research. Depending on the type of research being carried out, the present invention provides different functionality. For example, a research partner can use a template builder provided on one of the systems of the IPI 100 or Form Manager software to generate the case report forms (CRF) required to complete a clinical trial. The research functionality of the present invention can then be used to retrieve, complete, and submit that form using the RFD form management standard.

In that example, the research partner or the IPI provider uses the research functionality of the present invention to pre-populate much of the data in those forms using the data stored on the various systems of the IPI 100. Those pre-populated forms are then transferred to a clinical trial sponsor's or CRO's EDC system for completion via data capture at the point of care by an authorized physician, delegate, Principle Investigator (PI), and/or CRC conducting the clinical trial (i.e., the Form Filler). Rather than being retrieved, those documents may also be sent automatically to the EDC system based on a triggering event, such as a scheduled patient visit. After the forms are completed at the EDC system, they are submitted back to the clinical trial sponsor or CRO (i.e., the Form Receiver and/or Form Archiver) at an external information system 142 or at their research system within the IPI 100 for analysis and archiving.

Accordingly, the research functionality of the present invention streamlines data entry and shortens the time required by the authorized physician, delegate, PI, and/or CRC to complete those forms by allowing them to retrieve, complete, and submit the required forms within a single application. And, where the EDC systems has been integrated with the systems of the IPI 100, data captured during the clinical trials using those EDC systems can be captured in real time within the IPI 100 for use by the other systems of the IPI 100. Even where the EDC system is not integrated with the other systems of the IPI 100, the IPI 100 can be configured to consume that data.

In addition, the IPI 100 can also be configured to consume data from a CTMS. For example, the present invention can utilize the Retrieve Protocol for Execution Profile (RPE) integration standard to retrieve the clinical trial instructions (i.e., the trial protocol) from the CTMS system and execute them at the systems of the IPI 100 that will be used to capture data for the clinical trial (e.g., EHR systems). Accordingly, the RPE integration standard can be utilized to integrate site-based clinical research work flow into the task managers of EHR systems within the IPI 100 to automate scheduling and consume trial protocol documents. Thus, the RPE integration standard can be used to expand upon the amount system integration facilitated by the RFD form management standard. The RPE integration standard is currently maintained by the IHE and its contents are hereby incorporated by reference.

The present invention can also use the RFD form management standard to retrieve Adverse Event (AE) forms from local Institutional Review Boards (IRBs), to pre-populate data into those forms, and to submit those forms back to the IRBs, to the clinical trial sponsor or CRO, and to all other sites participating in the same clinical trial. AE forms are used to report adverse changes in health or side-effects that occur in a patient participating in a clinical trial while the patient is receiving treatment (e.g., receiving test medication, using a test medical device, etc.) or within a pre-defined period of time after their treatment is completed. And, because of the integrated functionality of the present invention, the completed AE forms can be quickly and efficiently completed and submitted to all of the necessary parties, particularly the other research sites participating in the clinical trial.

The present invention can also use the RFD form management standard to submit forms to various safety/quality organizations (e.g., MGMA, AHRQ, NCQA, HEDIS, CMS, etc.) that track the performance of specific healthcare providers and determine whether those healthcare providers have satisfied certain quality measures and therefore qualify for specific certifications, accreditations, and/or incentives. For example, a healthcare provider can utilize that functionality to pre-populate the forms required by CMS to qualify for Pay for Performance (P4P) incentive pay under the Physician Quality Reporting Initiative (PQRI). The healthcare provider then completes any part of the form not pre-populated by the present invention and submits it to CMS.

Where the systems of the IPI 100 contain all of the information required to complete specific forms and an IPI user need not complete any part of that form, the present invention can also be configured to send the defined data elements for each specific form to a central router or registry in a batch or near real time feed. That feed effectively completes the forms without any action by the IPI user other than capturing the required data. Accordingly, IPI users can complete forms in real time as data is collected, which the associated IPI system will automatically submit without any additional IPI user interaction. That functionality is particularly useful for quality initiatives that require physicians to regularly complete and submit identical forms on quality measures for a variety of covered services.

The present invention can also use the RFD form management standard to submit forms to various public health organizations based on certain triggering events. For example, when a user of an EHR system within the IPI 100 indicates that a child was born to a patient, that event will automatically trigger the EHR system to retrieve the required registration form from the local Department of Public Health. The EHR system will also pre-populate the form with the parent's demographic data, the baby's date of birth, and any other information captured by the EHR system, such as the baby's weight as measured by an electronic scale connected to the EHR system. After the registration form is complete by the EHR system user, the EHR system will automatically submit the completed form back the local Department of Public Health in a format easily recognized and processed by that Department of Public Health.

Using all of the functionality described above and equivalents thereof, the present invention provides an integrated system for quickly, accurately, and seamlessly collecting, tracking, and analyzing medical data across a vast patient population. The present invention also provides functionality for managing and coordinating care across a community of healthcare providers in different settings, which can reduce the costs of unnecessary emergency room visits, repeated lab tests, and preventable hospitalizations. The system is particularly suited for performing medical research because it provides infrastructure and functionality for utilizing that data to more effectively and efficiently perform medical research, maintain disease registries, track patient care for quality and safety initiatives, and perform composite clinical and financial analytics. Moreover, the infrastructure and functionality of the present invention facilitate the measurement and promotion of continued improvement in clinical care.

The foregoing description and drawings should be considered as illustrative only of the principles of the invention. The invention may be configured in a variety of shapes and sizes and is not intended to be limited by the preferred embodiment. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

What is claimed is:

1. A system for performing medical research over an extended computer network, the system comprising:

an enhanced services server built on the same architecture as a plurality of Electronic Health Record (EHR) systems, the plurality of EHR systems being configured to capture patient data for a plurality of general patients at a plurality of corresponding healthcare provider sites during encounters with those patients, said plurality of EHR systems being configured to capture and transmit the patient data in a common data format that specifies information to be collected and a format for the information to be collected, and the enhanced services server being in electronic data communication with the plurality of EHR systems and the one or more research systems via a network connection and being configured to transmit and receive the patient data in the common data format and to perform the steps of:

identifying a plurality of qualifying patients from among the plurality of general patients that qualify for the medical research;

electronically receiving the one or more electronic documents in the common data format from a research system via the network connection, the one or more electronic documents including one or more first fields and one or more second fields for completion with patient data that is related to the medical research;

automatically populating the one or more first fields in each of the one or more electronic documents with patient data in the common data format for a corresponding one of the plurality of qualifying patients, the patient data being related to the medical research and having been captured with at least one of the plurality of EHR systems during previous encounters with the plurality of qualifying patients;

electronically transmitting the one or more electronic documents that were automatically populated with patient data for each of the qualifying patients to at least one EHR system via the network connection, the at least one of the plurality of EHR systems being used to complete the one or more second fields in each of the one or more electronic documents with patient data related to the medical research during subsequent encounters with the plurality of qualifying patients;

electronically receiving the one or more electronic documents from the at least one EHR system via the network connection, the one or more electronic documents electronically received from the at least one of the plurality of EHR systems having the one or more first fields and one or more second fields completed; and electronically transmitting the one or more electronic documents with the one or more first fields and one or more second fields completed back to the research system via the network connection.

2. The system of claim 1, wherein the at least one of the plurality of EHR systems includes Electronic Data Capture (EDC) software for completing the one or more second fields in each of the one or more electronic documents.

3. The system of claim 1, wherein the research system is interfaced with the enhanced services server via an interoperability engine at the enhanced services server; and the patient data related to the medical research is made available to the research system in real time as it is captured with the at least one of the plurality of EHR systems.

4. The system of claim 1, wherein the one or more electronic documents are electronically transmitted, electronically received, electronically consumed, and automatically populated using the Retrieve Form for Data Capture (RFD) form management standard.

5. The system of claim 4, wherein the at least one of the plurality of EHR systems performs as a form filler under the RFD form management standard;

the research system performs as a form manager and a form archiver under the RFD form management standard; and the enhanced services server performs as a form filler and a form receiver under the RFD form management standard.

6. The system of claim 1, wherein the enhanced services server identifies the plurality of qualifying patients based on criteria received from the research system via the network connection.

7. The system of claim 1, wherein the enhanced services server is further configured to perform the steps of:

automatically populating consent forms with language required by the Health Insurance Portability and Accountability Act (HIPAA) regarding patient data that is protected under HIPAA; and electronically transmitting the populated consent form to the at least one of the plurality of EHR systems for receiving consent from the plurality of qualifying patients to access those patients' patient-specific information, wherein at least one of the plurality of qualifying patient's patient-specific information will not be automatically populated in the one or more first fields or the one or more second fields if consent is not received from that qualifying patient.

8. The system of claim 1, wherein the enhanced services server is further configured to perform the step of electronically transmitting the one or more electronic documents that were automatically populated with patient data for each of the qualifying patients back to the research system via the network connection; and the research system is configured to electronically transmit the one or more electronic documents that were automatically populated with patient data for each of the qualifying patients to one or more external systems for the one or more second fields to be completed and to receive the one or more electronic documents back from the one or more external systems with the one or more first fields and one or more second fields completed, the one or more external systems having EDC software for capturing patient data related to the medical research during subsequent encounters with the plurality of qualifying patients.

9. The system of claim 1, wherein the at least one of the plurality of EHR systems is further configured to automatically retrieve the one or more electronic documents for at least one of the plurality of qualifying patients at a scheduled time for a subsequent encounter with that qualifying patient, the one or more first fields in the one or more electronic documents retrieved for that qualifying patient being automatically populated with patient data for that at least one qualifying patient that is related to the medical research.

10. The system of claim 1, wherein
the research system includes Clinical Trials Management System (CTMS) software that generates clinical instructions for the medical research; and
the enhanced services server consumes the clinical instructions and integrates them into tasks performed with the at least one of the plurality of EHR systems to automatically schedule subsequent encounters with the plurality of qualifying patients.

11. The system of claim 10, wherein the Retrieve Protocol for Execution (RPE) integration standard is used to consume the clinical instructions and integrate them into tasks performed with the at least one of the plurality of EHR systems.

12. The system of claim 1, wherein the research system includes template builder and/or form manager software for creating the one or more electronic documents and defining the one of more first fields and one or more second fields in the one or more electronic documents.

13. A method for performing medical research over an extended computer network, the method comprising the steps of:
placing an enhanced services server in electronic data communication with a plurality of Electronic Health Record (EHR) systems and a research system via a network connection, the plurality of EHR systems being configured to capture patient data for a plurality of general patients at a plurality of corresponding healthcare provider sites during encounters with those patients, said plurality of EHR systems being configured to capture and transmit the patient data in a common data format that specifies information to be collected and a format for the information to be collected, and the enhanced services server being built on the same architecture as the plurality of EHR systems and configured to transmit and receive the patient data in the common data format;
using the enhanced service server to identify a plurality of qualifying patients from among the plurality of general patients that qualify for the medical research;
electronically receiving at the enhanced services server one or more electronic documents in the common data format from the research system, the one or more electronic documents including one or more first fields and one or more second fields for completion with patient data that is related to the medical research;
using the enhanced services server to automatically populate the one or more first fields in each of the one or more electronic documents with patient data in the common data format for a corresponding one of the plurality of qualifying patients, the patient data being related to the medical research and having been captured with at least one of the plurality of EHR systems during previous encounters with the plurality of qualifying patients;
electronically transmitting the one or more electronic documents that were automatically populated with patient data for each of the qualifying patients from the enhanced services server to the at least one of the plurality of EHR systems via the network connection;
using the at least one of the plurality of EHR systems to complete the one or more second fields in each of the one or more electronic documents with patient data related to the medical research during subsequent encounters with the plurality of qualifying patients;
electronically transmitting the one or more electronic documents from the at least one EHR system to the enhanced services server via the network connection, the one or more electronic documents electronically received from the at least one of the plurality of EHR systems having the one or more first fields and one or more second fields completed; and
electronically transmitting the one or more electronic documents with the one or more first fields and one or more second fields completed from the enhanced services server back to the research system via the network connection.

14. The method of claim 13, wherein the at least one of the plurality of EHR systems includes Electronic Data Capture (EDC) software for completing the one or more second fields in each of the one or more electronic documents.

15. The method of claim 13, further comprising the step of using the enhanced services server to make the patient data related to the medical research available to the research system in real time as it is captured with the at least one of the plurality of EHR systems, wherein the research system is interfaced with the enhanced services server via an interoperability engine at the enhanced services server.

16. The method of claim 13, wherein the one or more electronic documents are electronically transmitted, electronically consumed, and automatically populated using the Retrieve Form for Data Capture (RFD) form management standard.

17. The method of claim 16, wherein
the at least one of the plurality of EHR systems performs as a form filler under the RFD form management standard;
the research system performs as a form manager and a form archiver under the RFD form management standard; and
the enhanced services server performs as a form filler and a form receiver under the RFD form management standard.

18. The method of claim 13, wherein the enhanced services server identifies the plurality of qualifying patients based on criteria received from the research system via the network connection.

19. The method of claim 13, further comprising the steps of:
automatically populating consent forms with language required by the Health Insurance Portability and Accountability Act (HIPAA) regarding patient data that is protected under HIPAA; and
electronically transmitting the populated consent form to the at least one of the plurality of EHR systems for receiving consent from the plurality of qualifying patients to access those patients' patient-specific information,
wherein at least one of the plurality of qualifying patient's patient-specific information will not be automatically populated in the one or more first fields or the one or more second fields if consent is not received from that qualifying patient.

20. The method of claim 13, further comprising the steps of:
electronically transmitting the one or more electronic documents that were automatically populated with patient data for each of the qualifying patients from the enhanced services server back to the research system via the network connection;
electronically transmitting the one or more electronic documents that were automatically populated patient with data for each of the qualifying patients from the research system to one or more external systems for the one or more second fields to be completed;
completing the one or more fields in the one or more electronic documents with patient data related to the medical research during subsequent encounters with the plurality of qualifying patients, the one or more external systems having EDC software for capturing that patient data; and transmitting the one or more electronic documents from the one or more external systems back to the research system via the network connection, the one or more electronic documents transmitted back to the research system having the one or more first fields and one or more second fields completed.

21. The method of claim 13, further comprising the step of using the at least one of the plurality of EHR systems to automatically retrieve the one or more electronic documents for one of the plurality of qualifying patients at a scheduled time for a subsequent encounter with that qualifying patient, the one or more first fields in the one or more electronic documents retrieved for that qualifying patient being automatically populated with patient data for that qualifying patient that is related to the medical research.

22. The method of claim 13, further comprising the steps of:
    generating clinical instructions for the medical research with Clinical Trials Management System (CTMS) software at the research system; and
    using the enhanced services server to consume the clinical instructions and integrate them into tasks performed with the at least one of the plurality of EHR systems to automatically schedule subsequent encounters with the plurality of qualifying patients.

23. The method of claim 22, wherein the Retrieve Protocol for Execution (RPE) integration standard is used to consume the clinical instructions and integrate them into tasks performed with the at least one of the plurality of EHR systems.

24. The method of claim 13, further comprising the step of using template builder and/or form manager software at the research system to create the one or more electronic documents and define the one of more first fields and one or more second fields in the one or more electronic documents.

* * * * *